US007662371B2

(12) United States Patent
Brønstad et al.

(10) Patent No.: US 7,662,371 B2
(45) Date of Patent: Feb. 16, 2010

(54) COMPOSITION FOR LOWERING THE CONCENTRATION OF INTESTINAL PATHOGENIC PEPTIDES

(75) Inventors: Gunnar O. Brønstad, Snåsa (NO); Karl Ludwig Reichelt, Oslo (NO); Erik Slinde, Bergen (NO)

(73) Assignee: Neurozym Biotech AS, Snasa (NO)

( * ) Notice: Subject to any disclaimer, the term of this patent is extended or adjusted under 35 U.S.C. 154(b) by 193 days.

(21) Appl. No.: 10/491,291

(22) PCT Filed: Oct. 2, 2002

(86) PCT No.: PCT/NO02/00354

§ 371 (c)(1),
(2), (4) Date: Aug. 5, 2004

(87) PCT Pub. No.: WO03/028745

PCT Pub. Date: Apr. 10, 2003

(65) Prior Publication Data

US 2004/0247581 A1 Dec. 9, 2004

(30) Foreign Application Priority Data

Oct. 2, 2001 (NO) .................................. 20014788

(51) Int. Cl.
*A01N 63/04* (2006.01)
*A01N 65/00* (2006.01)
*A61K 39/02* (2006.01)
*A61K 39/38* (2006.01)
*A61K 47/00* (2006.01)

(52) U.S. Cl. ................. 424/93.45; 424/1.11; 424/78.01; 424/93.1; 424/93.3; 424/93.4; 424/184.1; 424/234.1; 424/278.1; 435/252.9

(58) Field of Classification Search ................ 424/1.11, 424/93.1, 93.2, 93.3, 93.4, 93.44, 93.45, 424/184.1, 234.1, 237.1, 278.1; 426/61, 426/68, 531, 664; 435/243, 252.3, 252.9
See application file for complete search history.

(56) References Cited

U.S. PATENT DOCUMENTS

| 4,879,213 | A |   | 11/1989 | Fox et al. |
| 5,310,555 | A | * | 5/1994  | Zimmer ....................... 424/438 |
| 5,494,664 | A | * | 2/1996  | Brassart et al. ............. 424/93.4 |
| 5,709,857 | A | * | 1/1998  | Morelli et al. ............. 424/93.45 |
| 6,022,568 | A | * | 2/2000  | Lesens et al. ................. 426/61 |

FOREIGN PATENT DOCUMENTS

| EP | 0 626 452 A1 | 11/1994 |
| EP | 0969015 | 1/2000 |
| WO | WO 96/41879 A1 | 12/1996 |

OTHER PUBLICATIONS

Fernandes et al. 1987. FEMS Microbiology Review. vol. 46: 343-356.*

Bernheimer et al., "Nature and Mechanism of Action of the Camp Protein of Group B *Streptococci*", *Infection and Immunity* 23(3): 838-844 (1979).
Burgess et al., *J. Cell Biol.* 111: 2129-2138 (1990).
Christie et al., "A Note on a Lytic Phenomenon Shown by Group B *Streptococci*", *Aus. J. Exp. Bio. Med. Sci.* 22: 197-200 (1944).
Fehrenbach et al., "Interaction of Amphiphilic Bacterial Polypeptides With Artificial Membranes", *Bacterial Protein Tokins*, pp. 317-324 (1984).
Fehrenbach et al., Role of Camp-Factor (Protein B) for Virulence, (eds.) *Bacterial Protein Toxins, Zbl. Bakt. Suppl.* 17: 351-357 (1988).
Finch et al,, "Further Studies on the Efficacy of a Live Vaccine Against Mastitis Caused by *Streptococcus uberis*", Vaccine. 15(10): 1138-1143, 1997.
Figura et al., "Differentiation of Motile and Mesophilic Aeromonas Strains Into Species by Testing for a Campo-Like Factor", *J. Clin. Microbiol.* 25(7): 1341-1342 (1987).
Fontaine et al., "Immunisation of Dairy Cattle With Recombinant *Streptococcus uberis* GAPC or a Chimeric Camp Antigen Confers Protection Against Heterologous Bacterial Challenge", Vaccine ;20:2278-2286, 2002.
Fontaine at al.. "Immunisation of Dairy Cattle With Recombinant *Strptococcus uberis* GAPC or a Chimeric Camp Antigen Confers Protection Against Heterologous Bacterial Challenge", Vaccine 20:3047-3048, 2002.
Fraser, Gordon. "Bacteriology: Haemolytic Activity of *Corynebacterium*", *Nature* 189: 246- (1961).
Frey et al., "Cloning and Expression of a Cohemolysin, The Camp Factor of *Actinobacillus pleuropneumoniae*", Infection & Immunity 57(7): 2050-2056(1989).
George et al., "Macromol Sequencing Synthesis", *Select Meth. Appl.* Alan Liss Inc. (1988).
Herzog et al., *DNA and Cell Biology*, 12(6): 465-471 (1993).
Jiang et al., "Cloning, Sequencing and Expression of The Camp Factor Gene of *Streptococcus uberis*", 20: 297-307 (1996).
Jurgens et al., "Purification and Characterization of Camp-Factor From *Streptococcus aglactiae* by Hydrophobic Interaction Chromatography and Chromatofocusing", *Journal of Chromatography*, 348: 363-370 (1985).
Jurgens et al., "Unspecific Binding of Group B *Streptococcal cocytoiysen* (Camp Factor) to Immunoglobins and Its Possible Role in Pathogenicity", *Exp. Med.* 165: 720-732 (1987).
Kohler, W. "Camp-Like Phenomena of Vibrios", *Zentralbl. Bakteriol. Mikrobiol. Hyg. Ser. A* 270: 35-40 (1988).
Lazar et al., *Mol. Cell. Biol.* 8(3): 1247-1252 (1988).
Leigh et al., "Vaccination With the Plasminogen Activator From *Streptococcus uberis* Induces an Inhibitory Response and Protects Against Experimental Infection in the Dairy Cow", Vaccine 17:851-857,1997.

(Continued)

Primary Examiner—Mark Navarro
Assistant Examiner—JaNa Hines
(74) Attorney, Agent, or Firm—Dobe Law Group, LLC; Christopher Aniedobe (57) ABSTRACT

The present invention describes a pharmaceutical, veterinary or alimentary composition comprising one or more bacterial strains capable of lowering the concentration of intestinal pathogenic peptides by means of peptidases of probiotic strains. The invention also relates to the use of such compositions, and a method for selection of probiotic strains. Also, the invention relates to novel bacterial strains.

11 Claims, 4 Drawing Sheets

OTHER PUBLICATIONS

Levinson et al., *Examination & Board Review, Medical Microbiology & Immunology* pp. 292-293 (1994).

Podbielski, *Med. Microbiol. Immunol.* 183: 239-256 (1994).

Rocourt et al., "Notes; *Listeria welshimeri* SP. Nov, and *Listeria seeligeri* SP. Nov." *International J. Syst. Bacteriol.* 33(4): 866-869 (1983).

Rudinger et al., "Peptide Hormones", *ed. Parsons University Park Press* (1976).

Ruhlmann et al., "Complete Amino Acid Sequence of Protein B", *Fed. Of Europ. Biochem. Soc.* 235 (1,2): 262-266 (1988).

Sambrook et al., "Expression of Cloned Genes in *E. coli*", *Molecular Cloning, A Laboratory Manual*, Chp. 17, *CSH* (1989).

Schneewind at al., "Cloning and Expression of the Camp Factor of Group B *Streptococci* in *Escherichia coli*", *Infection & Immunity* 56(8): 2174-2179 (1988).

Skalka et al., "Lethal Effect of Camp-Factor and Uberis-Factor-A New Finding About Diffusible Exosubstances of *Streptococcus agalactiae* and *Streptococcus uberis*", *Zentraibl. Bakteriol. Ser. A* 249:190-194 (1981).

Sterzik et al., "Interaction of the Camp-Factor from *S. agalactiae* with Artificial Membranes", *Bacterial Protein Toxins*, pp. 195-196 (1984).

Sterzik et al., "Structure and Function of Camp Factor of *Streptococcus agalactiae*", *Zentralbl. Bakteriol. Mikrobiol. Hyg. Abt. 1*, 15: 101-108 (1985).

Williams, *Lett. Appl. Microbiol.* 12(1): 23-28 (1991).

Meisel et al., "Bioactive peptides encrypted in milk proteins: proteolytic activation and thropho-functional properties," Antonie van Leeuwenhoek 1999; 76: 207-215.

Sanz et al., "Purification and Characterization of an X-Prolyl-Dipeptidyl Peptidase from *Lactobacillus sakei*," Applied and Environmental Microbiology 2001; 67: 1815-1820.

Brudnak, M.A., "Application of genomeceuticals to the molecular and immunological aspects of autism," Medical Hypothesis 2001; 57(2): 186-191.

Cornell et al., "The effect of gliadin peptides on rat-liver lysosomes in relation to the pathogenesis of coeliac disease," Clinica Chimica Acta 1973; 49: 181-188.

Sandine, W.E., "Roles of *Lactobacillus* in the Intestinal Tract," Journal of Food Protection 1979; 42(3): 259-262.

Matar et al., "Beta-Casomorphin 4 from Milk Fermented by a Mutant of *Lactobacillus helveticus*," Int. Dairy Journal 1996; 6: 383-397.

Fernandes et al., "Therapeutic role of dietary lactobacilli and lactobacillic fermented dairy products," FEMS Microbiology Reviews 1987; 46: 343-356.

International Search Report for PCT Application No. PCT/NO02/00354.

* cited by examiner

COMPOSITION FOR LOWERING THE CONCENTRATION OF INTESTINAL PATHOGENIC PEPTIDES

FIELD OF THE INVENTION

The present invention relates to a pharmaceutical, veterinary or alimentary composition comprising one or more bacterial strains capable of lowering the concentration of intestinal pathogenic peptides. The invention further relates to the use of such compositions for the prevention and/or treatment of a disease or disorders such as psychiatric disorders, such as autism, ADHD, mood disorder, schizophrenia, pervasive development disorder, bipolar mood disorder and depression, allergic disorders, celiac disease and multiple sclerosis. The invention also relates to a method for the selection of bacterial strains, and to novel isolated bacterial strains.

BACKGROUND OF THE INVENTION

The etiology and pathogenesis of schizophrenia, autism and the major mood disorders is still unclear. Genetic factors certainly play an important role in the development and pathogenesis of these disorders. However, environmental factors contribute, and a combination of the two most probably operates, as is often seen.

A typical example of such a combined genetic and dietary based disease is Føllings disease, in which a genetic defect in the metabolism of phenylalanine results in severe maldevelopment of the brain. Dietary reduction of phenylalanine intake, however, prevents the disease development provided it is started shortly after birth. Therefore, an intensive search for environmental factors is going on, the discovery of which could strongly improve therapy of these devastating diseases. Such environmental factors could be infectious or dietary, or even both.

About 20 ago F. C. Dohan (Dohan, F. C (1983), More on celiac disease as a model for schizophrenia, Biological psychiatry, 18; 561-564; and Dohan, F. C (1988), Genetic hypothesis of idiopathic schizophrenia: its exorphin connection, Schizophrenia Bull, 14:489-494) discussed a possible relation between celiac disease and schizophrenia. Celiac disease is an inflammatory bowel disorder due to intolerance to peptides derived from gluten proteins. This condition is occasionally accompanied by psychiatric and neurological symptoms. A relation between celiac diseases and psychiatric and neurological disease is further supported by several recent investigations (KnivsBerg, Ann-Mari, Wiig, Kirsti, Lind, G. Nødland, M., Reichelt, K. L (1990), Dietary Intervention in Autistic Syndromes Brain Dysfunct, 3, 315-327; KnivsBerg, A. M. Reichelt, K. L, G. Nødland, M., Høyen, T (1990), Autistic Syndromes and Diet: a follow-up study, Scandinavian Journal of Educational Research; 39, 223-236; Whitley, P., Rodgers, J., Savery, D. and Shattock, p. (1999), An gluten-free diet as an intervention for autism and associated disorders: perliminary findings., Autism; 3: 45-65; Hadjivassilou, M., Grunewald, R. A, Chattopadhyay, A. K et al (1998), Clinical, radiological, neurophysiological, and neuropathological characteristics of gluten ataxia. The Lancet: 352, 1582-1586).

In 1979, Panksepp (Panksepp, J. A neurochemical theory of autism Trends in Neuroscience 1979; 2: 174-177) proposed the opioid excess theory in which he suggested that disturbance of endogenous opioid is part of the pathogenesis in autism. At the same time K. L. Reichelt et al (Hole, K., Bergslien, A. A, Jørgensen, H. et al (1979) A peptide containing fraction in the urine of schizophrenic patients which stimulates opiate receptors and inhibits dopamine uptake. Neuroscience; 4:1883-1893) isolated biologically active peptides from the urine from schizophrenic patients. Drysdale (Drysdale, A. Deacon, R., Lewis, R. et al (1982) A peptide containing fraction of plasma of schizophrenic patients which binds to opiate receptors and induces hyperactivity in rats Neuroscience; 7: 1567-1574) found a peptide-containing fraction in plasma from schizophrenic patients that were found to bind to opiate receptors, which induced hyperactivity in rats. Both groups showed that the principles they isolated had opioid and dopaminergic activity. At the present time, the best-characterized peptides found to be elevated in psychiatric patients, are exorphins derived from gluten and bovine caseins.

Several studies show elevated peptide levels in the urine of autistic persons (Reichelt, K. L and Teigland-Gjerstad, B (1995) Decreased urinary peptide excretion in schizophrenic patients after neuroleptic treatment sychiatry Research, 58; 171-176; Shattock, P. and Savery, D. (1997) Evaluation of Urinary Profiles obtained from people with autism and associated disorderes. Part 1:Classification of subgroups http://osiris.ac.uk/autism/ps97.htm) The inventors of the present invention have confirmed the urinary peptide pattern in normal and autistic individuals, and found higher levels in the autistic children.

Gluten Derived Exorphins

During the last year it has become clear that exorphins, a class of biologically active short peptides are produced enzymatically from gluten proteins in the gut during digestion. (Fukodome et al 1993, 1996, Froetshel 1996). These peptides, which are 4-5 amino acids long, have opioid activity and are relatively specific for δ-receptors.

Some representative gluten exorphins have the following amino acid sequence:

Exorphin A5: Gly-Tyr-Tyr-Pro-Thr (SEQ. ID. No. 1)
Exorphin A4: Gly-Tyr-Tyr-Pro (SEQ. ID. No. 2)
Exorphin B5: Tyr-Gly-Gly-Trp-Leu (SEQ. ID. No. 3)
Exorphin B4: Tyr-Gly-Gly-Trp (SEQ. ID. No. 4)
Exorphin C: Tyr-Pro-Ile-Ser-Leu (SEQ. ID. No. 5)

DeSantis et al (1997) (DeSantis, A. et al (1997) Schizophrenic symptoms and SPECT abnormalities in a coeliac patient: regression after a gluten-free diet, Journal of internal medicine 242:421-423) has shown regression of schizophrenic symptoms and SPECT (Single Photon Computer Tomography) abnormalities in a celiac patient after a gluten-free diet. An involvement of gluten peptides in neurological diseases has recently been shown in celiac ataxia further supporting neuropathological effects of such substances (Hadjuvassilou et al 1998) (Hadjivassilou, M., Grunewald, R. A, Chattopadhyay, A. K et al (1998) Clinical, radiological, neurophysiological, and neuropathological characteristics of gluten ataxia. The Lancet:352, 1582-1586).

Furthermore, Wakefield 1998 (Wakefield, A. J., Murch, S H, Anthony, A. (1998) Ileal-lymphoid-nodular hyperplasia, non-specific colitis, and pervasive developmental disorder in children The Lancet 351: 637-641 and 2000) (Wakefield, A. J. Anthony A, Murch S H. (2000) Enterocolitis in Children With Developmental Disorders The American Journal of Gastroenerology 95: 2285-2295) has recently found a relation between ileal-lymphoid-nodular hyperplasia, non-specific colitis, and pervasive developmental disorder in a group of children. Reichelt et al, 1998, (Reichelt, W. H, Ek, J. Stensrud, M and Reichelt, K. L Peptide excretion in celiac disease. Journal of Pediatric gastroenterology and Nutrition, 1998; 26: 305-309) have demonstrated increased peptide excretion in celiac disease. Accordingly, the findings of gluten derived exorphins in the urine of patients with schizophrenia; autism and mood disorders strongly suggest a causal relation, further supported by dietary experiments.

The present invention is based on these findings, i.e. that some specific peptides are found at concentrations above normal, and that this is correlated to various disorders or symptoms. In order to prevent or treat such diseases it is thus anticipated that compositions capable of lowering this elevated peptide concentration should have an effect on the disease state.

Casomorphins

During the last decade it has also been demonstrated that peptide sequences derived from incomplete catabolism of milk proteins have opioid activity (Teschemacher, H., Koch, G., and Brantl, V. (1997) Milk Protein-Derived Opoid Receptor Ligands Biopol. 43: 99-117). Caseins degrade to peptides with 3-20 amino acids, some of which have opioid activity and are termed casomorphins.

Representative examples of the amino acid sequence of some casomorphins:

β-casomorphin 1-8: Tyr-Pro-Phe-Pro-Gly-Pro-Ile-Pro (SEQ. ID. No. 6);

β-casomorphin 1-7: Tyr-Pro-Phe-Pro-Gly-Pro-Ile (SEQ. ID. No. 7);

β-casomorphin 1-5: Tyr-Pro-Phe-Pro-Gly (SEQ. ID. No. 8);

β-casomorphin 1-4: Tyr-Pro-Phe-Pro (SEQ. ID. No. 9);

β-casomorphin 1-4 amide: Tyr-Pro-Phe-Pro-$NH_2$ (SEQ. ID. No. 9).

Recently, Sun et al (1999) (Sun, Z., Cade, J. R, Fregly, M. J. and Privette, R. M. (1999) β-casomorphin induces Fos-like immunoreactivity in discrete brain regions relevant to schizophrenia and autism., Autism; 3: 67-83) showed that β-casomorphin 1-7, which is one of the peptides isolated from the urine from patients with schizophrenia and autism that cause behavioral changes in rats. This peptide also induces Fos-like immunoreactivity in discrete brain regions relevant to schizophrenia and autism (Sun et al 1999).

Intact peptides can be absorbed from the small bowel. In humans it was demonstrated that bovine casein releases peptides that can pass to the blood during digestion of milk or yogurt (Chabance et al, 1998) (Chabance, B. Et al (1998) Casein peptide release and passage to the blood in humans during digestion of milk or yogurt, Biochimie, 80:155-165). In normal individuals, however, it appears that the peptidases in the gut and in the blood degrades such peptides rapidly (Teschemacher, H., Koch, G., and Brantl, V. (1997) Milk Protein-Derived Opoid Receptor Ligands Biopol. 43: 99-117). However, this seem not to be the case for patients suffering of the medical conditions described above, where it is believed that such an insufficient degradation or catabolism of these specific food derived peptides contribute to the development and severity of such diseases.

Clinical improvement in autistic children has been demonstrated in clinical trials following exclusion of either gluten or milk and milk products form the diet. (Reichelt, et al, 1990, Lucarelli 1995, Knivsberg et al, 1997, Whitley et al, 1999). In addition several causistic reports support the effect of gluten free and casein free diets in these patients.

Further, Singh and Kay reported in 1976 that wheat gluten could be a pathogenic factor in schizophrenia, and Reichelt et al (1990) have shown that a gluten-free diet effects the urinary peptide secretion and clinical state in schizophrenic patients.

Hyperpeptiduria, i.e. increased concentration of peptides in the urine, is regularly found in autism, schizophrenia and major depressive disorders (Reichelt, W. H, Knivsberg, A. M., Nødland, M., Stensrud, M. and Reichelt, K. L. (1997), Urinary peptide level and patterns in autistic children from seven countries, and the effect of dietary intervention after 4 years., Dev. Brain Dysfunct; 10: 44-55; Whitley, P., Rodgers, J., Savery, D. and Shattock, p. (1999), An gluten-free diet as an intervention for autism and associated disorders: perliminary findings. Autism; 3: 45-65; Reichelt, K. L., Sagedal, E, Landmark, J., Sangvik, B. T., Eggen, O., and Scott, H. (1990), The effect of gluten-free diet on urinary peptide secretion and clinical state in schizophrenia., Journal of Orthomolecular medicine, 5: 223; Reichelt, K. L., Ekrem, J. and Scott, H. (1990), Gluten, milk proteins and autism: dietary intervention effects on behavior and peptide secretion., Journal of applied nutrition; 42: 1-11; Sun, Z. And Cade, J. R (1999), A peptide found in schizophrenia and autism cause behavioral changes in rats. Autism; 3: 85-95; Wakefield, A. J. et al. (1998), Ileal-lymphoid-nodular hyperplasia, non-specific colitis, and pervasive developmental disorder in children, The Lancet 351: 637-641; Reichelt, K. L and Stensrud, M (1998) Increase in urinary peptides prior to the diagnosis of schizophrenia, Schizophrenia Research; 1998; 34: 211-213). The peptide pattern varies considerably between patients, which may be due to the presence of dietary peptides without biological effect, and not related to enzyme defects in the psychiatric diseases. However, even peptides without biological activity may act as peptidase inhibitors. During dietary treatment and after use of neuroleptic agents, urinary peptide patterns are normalized. Other gut-derived substances may also be involved, as Shattock has found that indoly-acryloylglycin (IAG) is present in the urine of autistic children, and Friedman discloses the presence of the nonhuman peptide dermorphin.

These findings indicate that there is a correlation between a concentration above normal for some specific peptides and the development of certain diseases, especially neurological disorders. Further, it is clearly established that some of these "pathogenic peptides" are derived from food proteins, e.g. caseins and gluten.

Further, there is evidence for genetic alterations in plasma dipeptidyl peptidase IV enzyme activity in depression and schizophrenia (Maes et al, 1994, 1996) (Maes, M., Goossens, F., Scharpe, S. et al (1994) Lower serum prolyl endopeptidase enzyme acivity in major depression: Further evidence that peptidases play allmenn role in the pathophysiology of depression. Biol. Psychiat.; 35: 545-552 Maes, M., Goossens, F., Scharpe, S. et al (1994) Lower serum prolyl endopeptidase enzyme acivity in major depression: Further evidence that peptidases play allmenn role in the pathophysiology of depression. Biol. Psychiat.; 35: 545-552), which may also affect intestinal enzyme activity. Defective metabolism of gut-derived peptides is reflected in the excretion pattern of such substances.

In conclusion, these investigations strongly support the idea that symptoms in such psychiatric disorders as schizophrenia, ADHD, autism and depressions, at least partly, result from incomplete breakdown and/or increased uptake of gut-derived peptides.

SUMMARY OF THE INVENTION

An object of the present invention is thus to lower the concentration of these "pathogenic peptides" by increasing the peptidase activity in the gut.

The term "pathogenic peptides" is intended to mean peptides involved in the development, progression or severity of a medical condition.

By the term "peptides" is meant peptides with a sequence of amino acids, preferable in the range of from 2 to 20 amino acids, and more preferable less than 10 amino acids.

It is important to emphasize that these food proteins first are degraded by proteinases to such peptides, and that another group of hydrolyzing enzymes, i.e. the peptidases, are responsible for the further degradation of these peptides to amino acids which functions as building blocks for protein synthesis.

A preferred embodiment of the invention relates to the lowering of the concentration of peptides derived from proteins contained in a diet, e.g. the food proteins gluten and casein.

The basic concept of the present invention is to use microorganisms capable of degrading such peptides in the gut.

A currently preferred embodiment of the present invention relates to the use of lactic acid bacteria. Preferable these bacteria contain peptidases capable of hydrolysing peptides by adhering to, and colonizing the gut mucosa. Furthermore, these peptidases may be released into the gut lumen by dead bacteria and thereby degrade unwanted peptides.

Biologically active peptides of the exorphin class can be broken down by various types of peptidases found both in animal cells and in microorganisms. In humans peptidases are found in most tissues, but intestinal and blood enzymes may be the most important in relation to the above-described psychiatric diseases.

The present invention thus relates to a mixture of one or more bacterial strains capable of degrading all kinds of unwanted peptides in the gut. A preferred embodiment of the present invention relates to a mixture of several bacteria, and where the combined peptidase effects have a substrate preference towards at least some of the above described peptides.

DETAILED DESCRIPTION OF PREFERRED EMBODIMENTS

Lactic Acid Bacterial Peptidase Systems

Lactic acid bacteria (LAB) inhabit a diverse range of environments such as the gut, various food and beverages such as dairy products, meat and wine as well as dead plant and animal materials. These bacteria can colonize the gut, and they play an important role for the normal gut function.

Some strains of LAB grow well in milk products, and are used extensively in the manufacturing of dairy products. Proteins and peptides can serve as sources for nitrogen, and are metabolized by several enzyme systems in the lactic acid bacteria, as reviewed by Pritchard and Coolbear (1993) Pritchard, G. G and Coolbear, T (1993) The physiology and biochemistry of the proteolytic system in lactic acid bacteria FEMS Microbiology Reviews 12: 170-206 and Yamamoto et al (1993) (angi fullstendige referanse Yamamoto, N. et al (1993) Purification and specificity of a cell-wall-associated proteinase from *Lactobacillus helveticus* CP790 J. Biochem, 114: 740-745

A protein hydrolysing enzyme (protease) is located in the bacterial cell wall of LAB, and is anchored to the plasma membrane. Casein for instance, is split into oligopeptide fragments with 3-20 or more amino acids by this enzyme.

Various strains of lactobacilli have different preferences for caseins, and the proteinases and peptidases of the bacteria have different substrate specificity. The proteinases from *L. Lactis* subsp. *cremoris* showed marked preference for δ-casein, while the proteinases from *L. Lactis* subsp. *lactis* degrades α- and β-casein.

The oligopeptide products of the proteinase action are taken up by specific transport systems and further degraded by several intracellular peptidases into di- and tripeptides and finally into amino acids. These amino acids are used in the synthesis of new bacterial proteins. This degradation process is quite well described for milk derived proteins, but less is known for the degradation of other diet proteins, e.g. gluten proteins.

In order to obtain bacteria capable of degrading the harmful peptides involved in the psychiatric disorders described above, the present inventors have searched for bacteria containing enzymes capable of providing an efficient degradation of these peptides. Such an effective degradation involves as indicated above several factors;

1) an efficient uptake system for such peptides, and
2) an effective internal catabolism of peptides by several peptidases acting together, and
3) release of peptidases by dying LAB and the external activity of the bacterial peptidases.

Since it appears that the enzymatic machinery in the gut is not sufficient to catabolize these short peptides that are involved in the psychiatric diseases referred to above, a main object of the present invention is to provide a composition capable of enhancing the peptide lowering activity, preferable in the intestine system.

Preferably, these pathogenic peptides should be broken down completely to amino acids. As shown in the experimental section we have tested several bacteria for the ability to degrade peptides postulated to be involved in said diseases. It is thus anticipated that by combining several strains of bacteria, preferably lactic acid bacteria we will obtain a peptidase mixture capable of eliminating these harmful peptides from the gut, and thus to alleviate and/or treat the manifested disease condition. Said composition of bacteria can possible also be used as a prophylactic agent for such disorders.

An object of the present invention is thus to identify a combination of bacteria, preferably LABs that meets these requirements. The representative bacteria described below are selected from healthy humans.

A further object of the present invention is to modulate various bacterial strains so that they exhibit the desired peptidase mixture, and the present invention thus also relates to genetic modified microorganisms.

The increased urinary excretion of peptides in psychiatric diseases appears to depend on an increased uptake from the gut. It is not known what is the primary cause for this, but a decrease in gut peptidases activity may explain the increased uptake. Whatever the cause is for the increased uptake of peptides in the gut, one must assume that the uptake depends on the level of peptides in the gut lumen. It is thus anticipated that the breakdown of pathogenic peptides in the gut will reduce the peptide uptake, and it is postulated that this will prevent and/or treat diseases caused by these peptides. Further, this will also appear as a reduced excretion of peptides in the urine.

The lactic acid bacterial peptidases in accordance to the present invention must be able to break down peptides such as casomorphins and gluteomorphins. It has been shown that *Lactobacillus casei* is able to hydrolyze casomorphin 1-7 in vitro by its aminopeptidase IV. High content of peptidases has been shown in various species of *Lactobacillus helveticus*.

The bacteria of the preset invention will be provided as a pharmaceutical or nutraceutical composition, and administered to a patient in need of such treatment, preferable as an oral composition or as a supplement agent in food products.

The bacterial strains must have properties that make them active in the intestinal system, by physically adherence and colonization, and by having efficient uptake mechanisms and high intracellular degrading capacity, such that the peptides are degraded rapidly in the gut after food intake. Release of peptidases to the intestinal lumen may further increase peptide degradation, either from living or dead bacteria.

A preferred embodiment of the invention provides bacteria that are capable of recolonizing the gut, at least for a limited period.

Further, it is essential that the bacterial strains used in accordance with the present invention are active in the intestinal environment that is characterized by low pH and high concentration of bile.

The preparations in accordance with the present invention may also be used in celiac disease and in allergic disorders, and other non-neurologic diseases. Both of these conditions involve reactions to foreign peptides and p'roteins. A complete or increased breakdown in the gut will eliminate or impede the uptake of disease promoting peptides, and could be used as a prophylaxis or treatment for the above indicated disorders.

A preferred embodiment of the present invention relates to a product being a capsule containing 2-4 strains of lyophilized living bacteria. Further preferred embodiments relates to a fermented milk preparation and to chewing tablets. The bacteria should have a preference for, and an enhanced degrading activity towards the pathogenic peptides in the gut.

Preferably, some of the bacterial strains contained in said preparation must be able to adhere to the mucosal surface, and grow and become part of the intestinal flora, and the product bacteria must retain their enzymatic activity in vivo.

Thus, the present invention relates to a pharmaceutical, veterinary or alimentary composition comprising one or more bacterial strains capable of lowering the concentration of intestinal pathogenic peptides.

Preferred embodiments relates to medical disorder or diseases behavioral or psychiatric disorders, such as autism, ADHD, mood disorder, schizophrenia, pervasive development disorder, bipolar mood disorder and depression, allergic disorders, celiac disease and multiple sclerosis.

Preferred embodiments relates to composition, wherein the composition comprises a *Lactobacillus* strain selected from the group comprising, Lb. *helveticus*, Lb. *acidophilus*, Lb. *lactis*, Lb. *casei, streptococcus, bifidobacterium* or *micrococcus*.

More preferred embodiments relates to bacterial strains selected from the group comprising *Lactobacillus crispatus* sp, *Lactobacillus para praracasei* sp, *Lactobacillus fermentum* sp, *Lactobacillus plantarum* sp and *Lactobacillus acidofilus*, and especially to the bacterial strains are selected from the group comprising NEU 458, NEU 421, NEU 480, NEU 401 and NEU 427.

The present invention also relates to the use of a composition for the preparation of a pharmaceutical or nutraceutical composition for the prevention and/or treatment of a disease or disorder caused or maintained by an elevated level of a (pathogenic) peptide in the intestine, wherein the composition comprising one or more bacterial strains capable of lowering the concentration of intestinal pathogenic peptides.

Representative diseases or disorders are selected from the group comprising behavioral or psychiatric disorders, such as autism, ADHD, mood disorder, schizophrenia, pervasive development disorder, bipolar mood disorder and depression, allergic disorders, celiac disease and multiple sclerosis.

The invention also relates to a method for the selection of bacterial strains capable of suitable for lowering the concentration of intestinal pathogenic peptides, wherein the various bacteria are selected based on the following steps:

a) determine the concentration of various peptides in a biological sample, for instance the urine or blood, b) determine if some of these peptides are involved as a causative agent in a medical disease or disorder, and c) select one or more bacterial strains that have shown preference for said peptide in an in vitro peptidase assay.

Further, the invention relates to the isolated bacterial strains NEU 458 and NEU 421 deposited on Sep. 26, 2002 at the DEUTSCHE SAMMLUNG VON MIKROORGANISMEN UND ZELLKULTUREN GmbH (DSMZ) Mascheroder Weg 1b 38124 Braunschweig Germany under number DSM 15224 and DSM 15223, respectively.

EXPERIMENTAL SECTION

This section contains experiments that demonstrate which properties probiotic microbial organisms need, in order to break down pathologic peptides in the gut lumen. All probiotic organisms must be safe. Effective probiotic organisms must contain peptidases that are able to hydrolyse the actual peptides with pathologic properties. In order to survive conditions in the stomach and the intestines they must be able to tolerate acidic conditions and bile acids. In order to have lasting effects they must be able to adhere to, and at least for some time colonise the mucosal surface. In addition microbial probiotic strains must grow well in a fermentor for production reasons.

The isolated probiotic strains presented in the invention were selected from bacteria isolated from epithelial cells from the urogential or gastrointestinal system. Cell samples were obtained from healthy human donors. Initially the bacterial samples were grown anaerobically on MRS agar plates. Cloned bacteria were sytematically tested for the properties described elsewhere in the specification. The selected probiotic strains were classified as lactic acid bacteria, since they were gram-positive, produce acid when they were grown, and they grew in the presence of 0.02% $NaN_3$. Bacteria that were classified as lactic acid bacteria were tested by the comerially available API-test to determine the strain. In this comercial test obtained from Biomerieux, which describes the fermetation pattern of carbohydrate substrates, we used the API 50 CH version.

Bacterial Strains

All lactic acid bacterial strains were grown from stocks stored at −84° C. (in 30% glycerol). The strains were grown in Man, Rogosa and Sharpe (MRS, Merck) broth at 37° C. Before testings the strains were replated 3 times.

Radio Labelling for Adhesion Assay

For metabolic radio labelling 40 µl $^3$H-adenine was added to a 20 ml bacterial suspension in MRS broth and incubated for 16-18 hs. To remove the excess radiolabel after growth, bacteria were centrifuged (2000 rpm) and the pellet was washed twice with phosphate buffered saline (PBS, pH 7.2). The optical density at 600 nm of the bacterial suspension was adjusted to 1.0 to give approximately between $6 \times 10^8$ and $2 \times 10^9$ colony forming units (CFU) $ml^{-1}$.

Caco-2 Cell Culture

The Caco-2 cell line (ATCC CRL-2102) was purchased from the American Type Culture Collection. The cells were cultured in RPMI 1640 supplemented with 10% fetal bovine serum and 2 mM L-glutamine and 1% penicillin/streptomycin at 37° C. in an atmosphere of 5% $CO_2$/95% air.

For adherence assays Caco-2 cells were grown in 96-well tissue culture plates. Cells were seeded at a concentration of $3 \times 10^4$ cells $ml^{-1}$ (200 µl in each well) and maintained for two weeks prior to use in adherence assays. The cell culture medium was changed every other day, in addition to two hours before adherence assay.

HEp-2 Cell Culture

HEp-2 cells were obtained from the ATCC and they were originally isolated from a patient with a larynx carcinoma. This cell line has been used extensively as a model in bacterial adherence studies. The cells were cultured in 75 cm² flasks in Dulbecco's modified Eagle's medium with 4 mM L-glutamine, adjusted to contain 4.5 g/L glucose, 1.5 g/L sodium bicarbonate, 1.0 mM sodium pyruvate, 10% fetal calf serum (FBS) and 1% penicillin/streptomycin at 37° C. in an atmosphere of 5% $CO_2$/95% air.

HEp-2 cells were cultured to confluency. The cells were trypsinated 48 hours before adherence experiments and seeded in 96-well microtiter plates with 200 µl per well from a cell suspension with $2.5 \times 10^5$ cells/ML giving $5 \times 10^4$ cells per well.

In Vitro Adherence Assay

The adherence of bacterial strains to Hep-2 or Caco-2 cell cultures was examined by adding 200 µl of radio labelled bacterial suspension to the wells. Before adding the bacteria they were suspended in MEM-Earle supplemented with 0.5% FBS, 1% L-glutamine and 0.1% NEA, all wells were washed twice with this medium. After incubation for 1-3 hours the Caco-2 cell culture were washed with $3 \times 250$ µl buffer saline solution (BSS) in a Multiwash$^+$ plate washer (Labsystems) and treated with 150 µl of 2% SDS in 0.01 M NaOH for 20 minutes to lyse the bacteria. The lysed bacteria were then mixed with scintillation liquid and the radioactivity was measured by liquid scintillation. The adhesion ratio (%) was calculated by comparing the radioactivity of the original bacterial suspension that was added to the final count of lysed cells.

Peptidase Activity

Using pNA labelled substrates, the peptidase activity of various bacterial strains was tested. The bacteria were harvested in the late log phase, and used to make a bacterial cell free extract containing peptidases. The peptidase extract were incubated with the labelled substrates, and the reaction was visible as a change in colour. The peptidase activity were calculated and given as nmol product per min per mg protein The bacteria were harvested in the late log phase by centrifugation at 7500 g at 4° C. for 10 minutes. After washing twice with 50 mM Hepes pH 7.0, containing 15 mM $CaCl_2$ to prevent autoprotolysis, the bacterial cells were resuspended in 50 mM HEPES buffer pH 7.0 without calcium. Bacterial cell free extract was obtained by first freezing and thawing the cells 3 times, then disrupting the cells by sonication at 4° C. for 5 minutes and centrifuged at 15 300 rpm at 4° C. for 10 minutes. The peptidase extract was kept at −20° C. maximally 3 weeks, until it was used in experiments. The amount of protein was determined with BCA protein kit at 562 nm.

The reaction between the substrate and the peptidase took place in 300 µl micro wells (NUNC) at 37° C. The colour change of a mixture of 100 µl of substrate and 100 µl of the peptidase extract was followed for with an automatic microplate reader at 414 nm using the Genesis Software.

Uptake and Metabolism of Peptides by Lactic Acid Bacteria

The bacteria were harvested in the late log phase by centrifugation at 7500 g at 4° C. for 10 minutes. Before the transport assays were performed, cells were washed twice with 100 mM MES-KOH (potassium-2-(N-morpholino)-ethanesulphonic acid), 2 mM $CaCl_2$, pH 6.5 (all buffers at a temperate at 4° C.). Cells ($A_{660}$=25) were de-energized with 10 mM 2-deoxyglucose for 20 min at 37° C., and washed twice with 100 mM MES-KOH, pH 6.5.

For transport assays, cells ($A_{660}$=10) were pre-incubated for 3 min in MES-KOH, with 25 mM glucose, after which 0.5 mM peptide was added.

The solution of peptides and bacteria was incubated at 37° C. Samples were taken after 0, 5, 10, 15, 30, 60 and 120 minutes. The cells were removed by centrifugation, and the supernatants were analysed using RP-HPLC.

The intracellular peptides were extracted, by adding 300 µl of a suspension of 5% perchloric acid and 10 mM Na-EDTA to the pellet, and incubated for 30 minutes. From this suspension, 110 µl was transmitted to an eppendorf tube with 100 µl 1 M KOH-$KHCO_3$.

The samples (100 µl) were analysed on an ÄKTA Purifier from Pharmasia Biotech, with a UV-900 detection unit, using a Vydac 218TP54 C-18 column. The peptides were eluted with a gradient from 0-35% B, in 100 minutes. Buffer A was 0.1% TFA in water, and buffer B was 0.1% TFA in 60% acetonitrile. The flow rate was 1 ml/min and the peptides were detected at 215 nm.

Uptake of Peptides in Caco-2 Cells

Caco-2 cells were used as an intestinal model system. A 24 well micro plate was used. A Lb. *acidophilus* were added to half of the wells. This is a lactic acid bacterium that adhere to the Caco-2 cells. All the wells were supplemented with β-casomorphine-7, and the concentration of β-casomorphine-7 was established at time 0, 60 and 120 minutes after addition of the peptide.

The wells were washed twice with 500 µl 0.5% serum medium without antibiotics. All the medium was removed from the wells before the bacteria/medium was added and incubated for one hour at 37° C. in an atmosphere of 5% $CO_2$/95% air. The wells were washed four times with BSS. The peptide (0.25 mM) was added in a medium without antibiotics and serum The samples (100 µl) were analysed on an ÄKTA Purifier from Pharmasia Biotech.

Results

The Table I below shows some bacterial stains which can be used as probiotic stains according to the invention.

TABLE I

Characterisation of selected probiotic strains by API C50 testing

| Bacterial strain | Identity by API testing |
| --- | --- |
| NEU 458 | *Lactobacillus crispatus* sp |
| NEU 421 | *Lactobacillus para praracasei* sp |

TABLE I-continued

Characterisation of selected probiotic strains by API C50 testing

| Bacterial strain | Identity by API testing |
|---|---|
| NEU 480 | Lactobacillus fermentum sp |
| NEU 401 | Lactobacillus plantarum sp |
| NEU 449 | Lactobacillus crispatus sp |

In Vitro Adherence Assay

Several bacterial strains were tested for the ability to adherence to Caco-2 cell lines. The capabilities of adhesion of some bacteria are given in Table II, below.

TABLE II

Examples of adhesion to cultured Caco-2 cells for some lactic acid bacteria

| Bacterial strain | Adhesion % |
|---|---|
| NEU 458 | 13 |
| NEU 480 | 22 |
| NEU 421 | 44 |
| NEU 449 | 42 |
| NEU 401 | 11 |
| NEU 427 | 49 |
| Lactobacillus GG | 12 |
| Lb Helveticus AL2 | 1 |
| Lb Helveticus ATCC 15009 | 1 |

Adherence experiments using the HEp-2 cells gave similar results, data not shown.

Peptidase Activity

Several bacterial strains were tested for peptidase activity against the Gly-Pro-pNA substrate, which gives an indication on the PepX activity. The example of peptidase activity of some bacteria is given in Table III, below.

TABLE III

Examples of peptidase activity for some lactic acid bacteria with various chromogenic substrates

| Strain | NEU458 | NEU480 | NEU421 | NEU427 |
|---|---|---|---|---|
| Substrate | | | | |
| Gly-Pro-pNA | 50.9 | 10.5 | 18.1 | 7.6 |
| Gly-pNA | 8.6 | 1.6 | 2.3 | 0.5 |
| Pro-pNA | 7.0 | 0 | 2.8 | 2.7 |
| Phe-Pro-Ala-pNA | 16.5 | 0 | 7.4 | 4.6 |
| Ala-Phe-Pro-pNA | 19.7 | 2.5 | 6.0 | 3.1 |

| Strain | NEU427 | NEU449 | Helv AL2 | Helv 15009 |
|---|---|---|---|---|
| Substrate | | | | |
| GlyPro-pNA | 7.6 | 35.2 | 30 | 64 |
| Gly-pNA | 0.5 | 4.1 | 5.7 | 5.5 |
| Pro-pNA | 1.9 | 4.1 | 5.6 | 4.2 |
| Phe-Pro-Ala-pNA | 4.6 | 9.3 | 15 | 20 |
| Ala-Phe-Pro-pNA | 3.1 | 21.7 | 10 | 13 |

Transport Assay

Uptake and degradation of the peptides dermorphin, β-casomorphin-8, β-casomorphim-7 and exorphin A5 have been studied in two Lb. helveticus bacteria and one Lb. acidophilus. Table IV shows the ability of various bacterial strains to degrade some specific peptides.

TABLE IV

Examples of uptake and degradation of peptides by some lactic acid bacteria.

| | Peptide | | | |
|---|---|---|---|---|
| Bacterial Strain | Dermorphin | β-casomorphin 8 | β-casomorphin 7 | Exorphin A5 |
| Lb. helveticus ATCC 15009 | 208.7 | 61.1 | 24.4 | 25.6 |
| Lb. helveticus AL 2 | | | 386.6 | 9.6 |
| Lb. acidophilus | | | 35.2 | |

Figure 1:
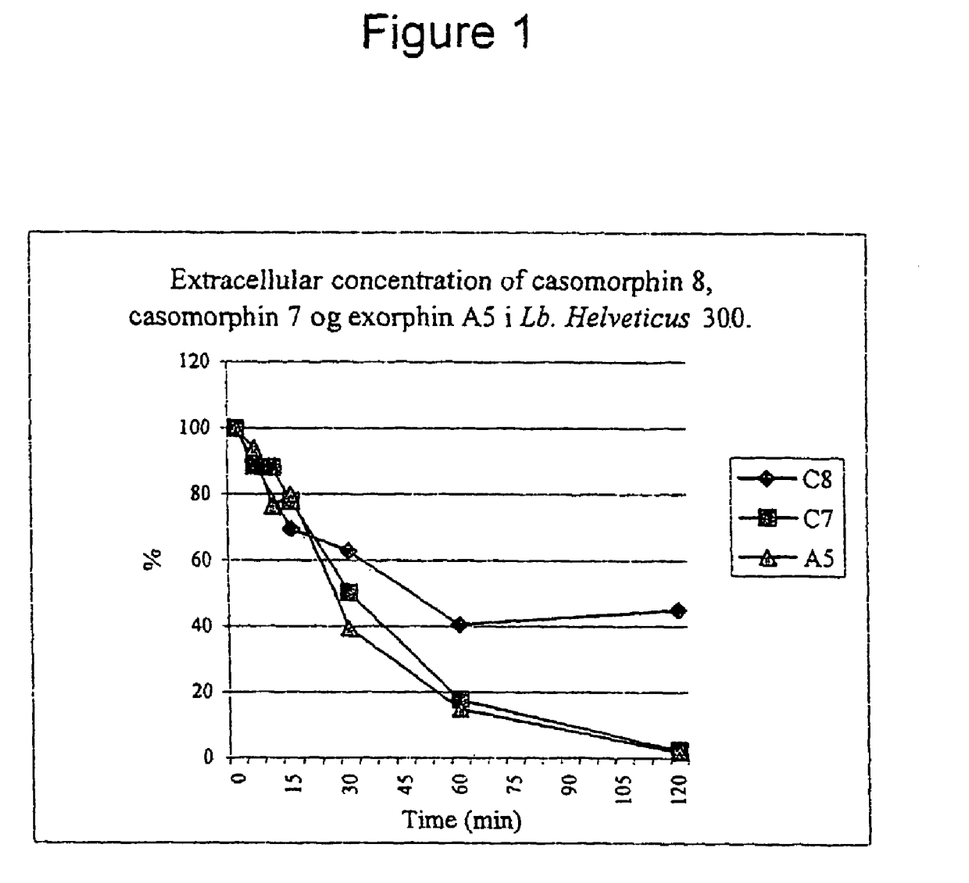
FIG. 1 shows the extra cellular degradation of β-casomorphin 8, β-casomorphin 7 and exorphin A5 in *Lactobacillus helveticus* ATCC 15009. The concentration at 0 minute equals 100%.
Figure 2:
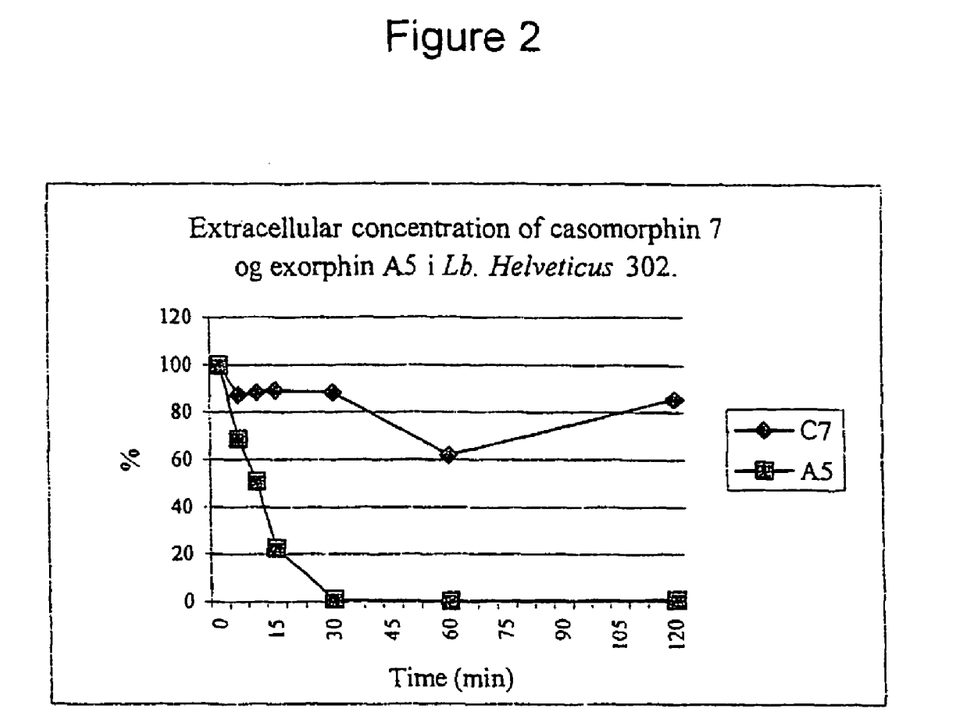
FIG. 2 shows the degradation of β-casomorphin 7 and exorphin A5 in *Lactobacillus helveticus* AL2. The concentration at 0 minute equals 100%.

Some of the results given in Table 3 are summarised in FIGS. 1 and 2. FIG. 1 shows the extra cellular degradation of β-casomorphin 8, β-casomorphin 7 and exorphin A5 in Lb. helveticus ATCC 15009. The concentration at 0 minute equals 100%.

Lb. helveticus degrades the three peptides very fast, even though the peptides have different amino acid sequences. This corresponds with the observation that this bacterium contains several peptidases giving combined broad substrate specificity (Table 3). FIG. 2 shows the degradation of β-casomorphin 7 and exorphin A5 in Lb. helveticus AL2. The concentration at 0 minute equals 100%.

This bacterium too had high activity towards the substrate Gly-Pro-pNA (Table 3): This bacterium has the highest activity towards the exorphin A5.

This examples show that the peptidase content is reflected in the ability pf intact cells to metabolise peptides, however, indicating the complexity.

Figure 3:
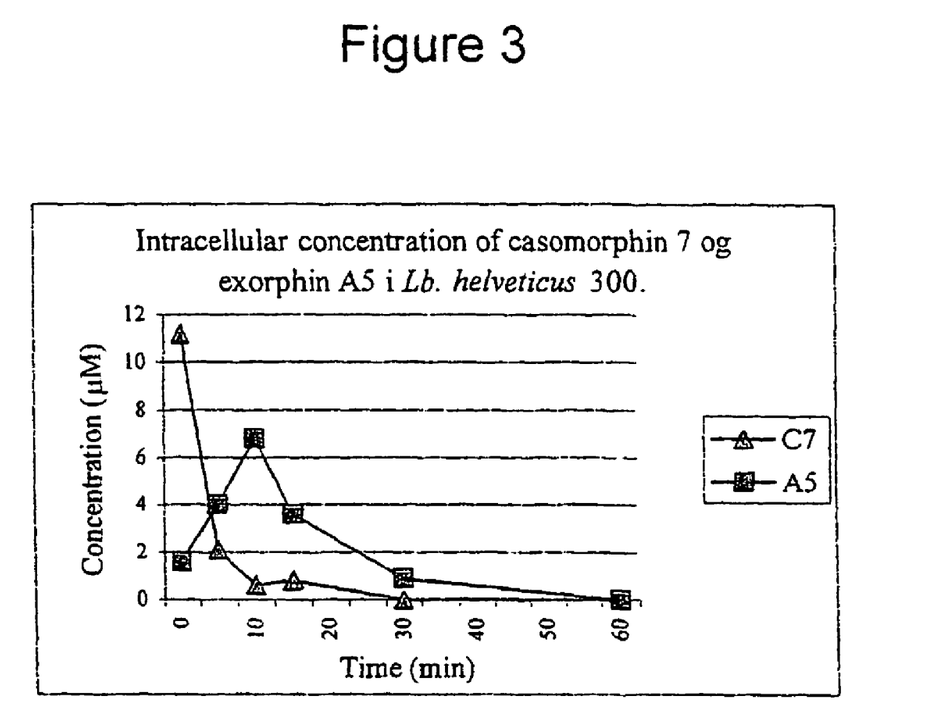
FIG. 3 shows the intracellular concentration of β-casomorphin 7 and exorphin A5 in *Lactobacillus helveticus* 300.

2-deoxy-glucose was used to empty the bacteria for amino acids and peptides, and it was anticipated that the intracellular peptides present were derived from the supplemented peptides. FIG. 3 shows the intracellular concentration of β-casomorphin 7 and exorphin A5 in Lb. helveticus 300.

Uptake of Peptides in Caco-2 Cells

The concentration of β-casomorphin-7 was lowered more quickly in an environment where a Lb. acidophilus was incubated together with the Caco-2 cells than in an environment without these bacteria.

Table 4 shows the concentration (μM) of β-casomorphin-7 when Caco-2 cells were incubated with or without Lb. acidophilus.

TABLE V

Concentration of β-casomorphine-7 incubated with and without Lb. acidophilus.

| | 0 | 60 | 120 |
|---|---|---|---|
| With Lb. acidophilus | 330.3 | 117.1 | 123.7 |
| Without Lb. acidophilus | 294.4 | 245.4 | 171.7 |

Figure 4:
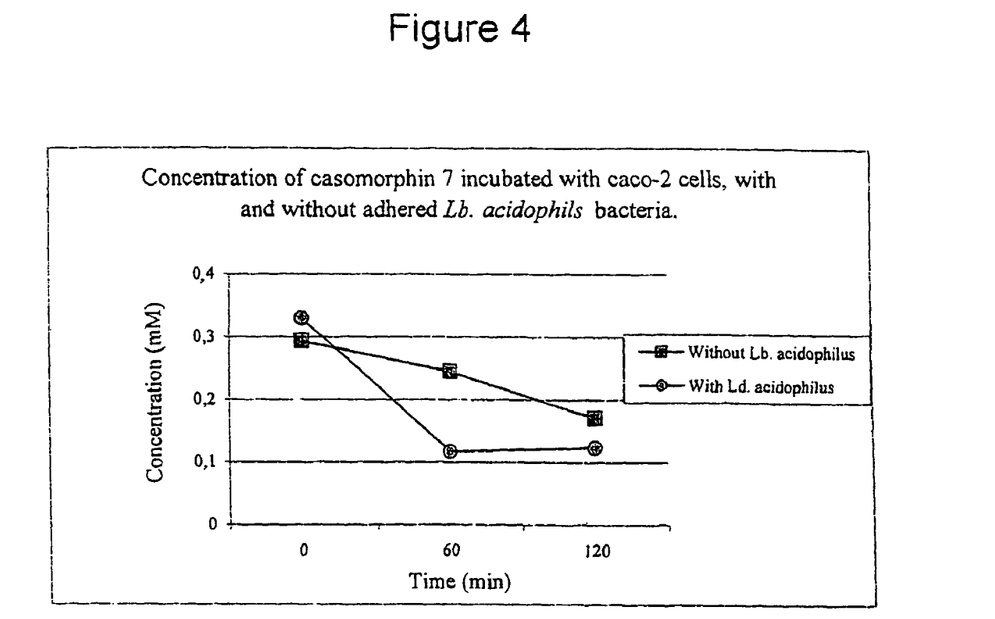
FIG. 4, which shows the extracellular concentration of β-casomorfin 7 in the culture medium of Caco-2 cells with and without an adhered probiotic strain.

These results are also shown in FIG. 4, which shows the extracellular concentration of β-casomorfin 7 in the culture medium of Caco-2 cells with and without an adhered probiotic strain. This finding supports the idea of the present invention, that probiotic bacteria adhered to intestinal cells may increase the breakdown of pathological peptides.

Discussion

Substantial evidence indicate that diet derived opioid peptides are involved in the pathogenesis of autism and other psychiatric diseases, and a reduction of the peptide level in the gastrointestinal tract has been shown to reduce symptoms in such patients. Furthermore, in autistic individuals gastrointestinal symptoms are frequently observed.

Oral treatment with vancomycin led to an improvement in 8 of 10 children indicating a role for some bacterial agent (Sandler R H, Finegold S M Bolte E R et al Short term benefit from oral vancomycin treatment of regressive-onset autism. J is Child Neurol, 2000; 15: 429-35)

In a recent study (Finegold, S M, Molitoris, D, Song, Y et al. Clinical Infectious Diseases 2002; 35 (Suppl 1)S6-16) it was found that the gastrointestinal microflora was disturbed in individuals with late onset autism.

The high adherence capacity combined with bile tolerance of the probiotic strains selected according to the present invention will re-establish the microflora in this patient group.

In order to support the claimed invention a range of lactic acid bacteria were isolated from human epithelial cells. Bacterial strains were selected based on several criteria such as identity as lactic acid bacteria, adherence to cultured Caco-2 cells, peptidase content, and bile tolerance.

The strains presented in Table I all grew well anaerobically in MRS-medium, and were all gram positive, acid producing and grew in the presence of azide. They were classified using the APICH50 fermentation system.

A prerequisite for colonisation of a mucosal surface is the capability to adhere to the cells of the epithelial surface. It is well documented that the human epithelial cell line Caco-2 expresses specific intestinal properties such as surface microvilli, enzyme systems transport mechanisms when cultured for 2 weeks. Thus, this cell line has been used extensively as a model system to study bacterial adherence. The bacterial strains selected in the present invention all show a very high degree of adherence to this cell line ranging from 11-49%. 2 comercially available leveticus strains had very low adherence capacity, below 2% and the extensively studied probiotic strain *Lactobacillus casei* GG had an adherence capacity of about 12%. All the strains presented could grow in the presence of bile. We therefore conclude that the probiotic strains presented in Table I meet the criteria commonly used to be able to colonise the human gut.

The objective of the present invention is to create a product which can reduce the level of harmful peptides in the gut. Such peptides are mainly supposed to derive from food proteins such as casein and gluten, but may also originate from microorganisms. Lactic acid bacteria used in the dairy industry has been extensively studied, but these bacteria do not colonise the gut, and can therefore not be used as human probiotics.

During the characterisation of strains isolated from human epithelial cells, we found a large variation in the peptidase content among actively adhering strains. Indeed we have selected bacteria with high activity of peptidases necessary to hydrolyse peptides of the exorphin type. X-prolyl-dipeptidyl peptiase, PepX, liberates XaaPro (dipeptides were the penultimat amino acid is prolin) dipeptides from the N-terminal end of peptidides containing from 3 to 7 amino acids.

The specific enzyme activities with various chromogenic substrates are shown in Table III. The values presented in the table are given as nmol product produced per minute and mg protein.

Gly-Pro-pNA reflects the activity of PepX, and as most exorphins derived form both casein and gluten contain several proline residues, this enzyme therefore will inactivate most of them. The strains presented in this table all actively hydrolysis this substrate. Gly-pNA liberates singel amino acids from the N-terminal end, and is a measure of PePC activity or PeP N activity. The strains presented in Table II all are able to hydrolyse Gly-pNA.

Pro-pNA reflects imini prolidase activity. This enzyme splits Xaa-Pro dipeptides, and activates products formed during the action of PePX. The selected strains have this enzyme activity. The four strains also hydrolyse both Phe-Pro-Ala-pNA and Ala-Phe-Pro-pNA, further supporting the peptide hydrolysing capacity of the isolated probiotic strains.

A combination of the lactic acid bacterial strains selected in this invention contains a peptidase combination able to break down the exorphins efficiently. Furthermore the broad spectrum peptidase activity of this combination of probiotics will be able to hydrolyze a broad range of food derived peptides, which will include toxic gliadin peptides causing celiac disease. A recent publication supports this idea (Di Cagno R, De Angelis M, Layermicocca P, De Vincezi M, Giovannini C, Faccia M, Gobetti M. Proteolysis by sourdough lactic acid bacteria: effects of wheat flour protein fractions and gliadin peptides involved in human cereal intolerance Appl Environ Microbiol; 68:623-633)

Enzyme preparations of selected lactobacilli showed hydrolysis of the 31-43 fragment of A-gliadin, a toxic peptide for celiac patients. This strongly supports our idea of using live lactic acid bacteria both containing necessary peptidases and being able to colonize the gut mucosa.

The probiotic strains selected in the present invention may indeed also be used as ingredients of an enzyme product. Such a product would be effective by enzymes acting in the gut content, but also by bacterial cell components adhering to the epithelial surface, as it has been found that peptidase activity may also be associated with the bacterial cell wall or membrane.

The invention claimed is:

1. A pharmaceutical or nutraceutical composition comprising one or more bacterial strains capable of adhering to walls of an intestine and lowering the concentration of one or more pathogenic peptides found in the intestine, wherein said bacterial strains are selected from the group consisting of DSM 15224 and DSM 15223.

2. The composition of claim 1, further comprising one or more lactic acid bacterial strains.

3. The composition of claim 2, wherein said lactic acid bacterial strain is selected from the group consisting of, *Lactobacillus helveticus, Lactobacillus acidophilus, Lactobacillus lactis, Lactobacillus casei, Lactobacillus crispatus, Lactobacillus paracasei, Lactobacillus fermentum*, and *Lactobacillus plantarum*.

4. The composition of claim 1, wherein the composition further comprises one or several genetically modified bacterial strains.

5. The composition in accordance with claim 2, wherein at least one of the bacterial strains has the following properties:
 a) maintain stability and exhibit peptidase activity in the intestine,
 b) resistance to proteolytic degradation
 c) active at the acidic environment of the intestine,
 d) resistance to intestinal bile acids.

6. The composition in accordance with claim 2, wherein at least some of the bacteria have the ability to colonize the intestinal epithelium.

7. The composition according to claim 2, wherein one of said bacterial strains is capable of colonizing and growing in the intestinal mucosa.

8. The composition according to claim 1 or claim 2, wherein said bacterial strains are present in lyophilized form.

9. The composition according to claim 1 or claim 2, wherein said composition is in the form of capsules, solutions or drinkable suspensions.

10. The composition according to claim 1, wherein said composition contains from $10^7$ to $10^9$ cells of each strain per single dose.

11. The composition of claim 1, wherein said bacterial strains further comprises at least one strain selected from the group consisting of *Streptococcus, Bifidobacterium* and *Micrococcus* strains.

* * * * *

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Protein degradation products

```
<400> SEQUENCE: 1

Gly Tyr Tyr Pro Thr
1               5

<210> SEQ ID NO 2
<211> LENGTH: 4
<212> TYPE: PRT
<213> ORGANISM: Artificial Sequence
<220> FEATURE:
<223> OTHER INFORMATION: Protein degradation product

<400> SEQUENCE: 2

Gly Tyr Tyr Pro
1

<210> SEQ ID NO 3
<211> LENGTH: 5
<212> TYPE: PRT
<213> ORGANISM: Artificial Sequence
<220> FEATURE:
<223> OTHER INFORMATION: Protein degradation product

<400> SEQUENCE: 3

Tyr Gly Gly Trp Leu
1               5

<210> SEQ ID NO 4
<211> LENGTH: 4
<212> TYPE: PRT
<213> ORGANISM: Artificial Sequence
<220> FEATURE:
<223> OTHER INFORMATION: Protein degradation product

<400> SEQUENCE: 4

Tyr Gly Gly Trp
1

<210> SEQ ID NO 5
<211> LENGTH: 5
<212> TYPE: PRT
<213> ORGANISM: Artificial Sequence
<220> FEATURE:
<223> OTHER INFORMATION: Protein degradation product

<400> SEQUENCE: 5

Tyr Pro Ile Ser Leu
1               5

<210> SEQ ID NO 6
<211> LENGTH: 8
<212> TYPE: PRT
<213> ORGANISM: Artificial Sequence
<220> FEATURE:
<223> OTHER INFORMATION: Protein degradation product

<400> SEQUENCE: 6

Tyr Pro Phe Pro Gly Pro Ile Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Protein degradation product
```

```
<400> SEQUENCE: 7

Tyr Pro Phe Pro Gly Pro Ile
1               5

<210> SEQ ID NO 8
<211> LENGTH: 5
<212> TYPE: PRT
<213> ORGANISM: Artificial Sequence
<220> FEATURE:
<223> OTHER INFORMATION: Protein degradation product

<400> SEQUENCE: 8

Tyr Pro Phe Pro Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Protein degradation product

<400> SEQUENCE: 9

Tyr Pro Phe Pro
1
```